(12) United States Patent
Tubel

(10) Patent No.: US 6,913,079 B2
(45) Date of Patent: Jul. 5, 2005

(54) METHOD AND SYSTEM FOR MONITORING SMART STRUCTURES UTILIZING DISTRIBUTED OPTICAL SENSORS

(76) Inventor: Paulo S. Tubel, 118 E. Placid Hill, The Woodlands, TX (US) 77381

( * ) Notice: Subject to any disclaimer, the term of this patent is extended or adjusted under 35 U.S.C. 154(b) by 0 days.

(21) Appl. No.: 10/312,235

(22) PCT Filed: Jun. 26, 2001

(86) PCT No.: PCT/US01/41165

§ 371 (c)(1),
(2), (4) Date: Dec. 23, 2002

(87) PCT Pub. No.: WO02/057805

PCT Pub. Date: Jul. 25, 2002

(65) Prior Publication Data

US 2003/0094281 A1 May 22, 2003

Related U.S. Application Data

(60) Provisional application No. 60/214,900, filed on Jun. 29, 2000.

(51) Int. Cl.$^7$ .......................... E21B 47/00; G01V 8/16; G01N 21/84
(52) U.S. Cl. .................... 166/250.01; 250/256; 356/72; 356/301; 114/382
(58) Field of Search .......................... 356/72, 326, 328, 356/301; 250/256; 73/152.39, 152.54; 166/250.01; 114/382; 246/1 R, 1 C, 120

(56) References Cited

U.S. PATENT DOCUMENTS

| | | | | |
|---|---|---|---|---|
| 4,703,175 A | * | 10/1987 | Salour et al. | ................. 356/45 |
| 4,714,342 A | * | 12/1987 | Jackson et al. | ................ 356/44 |
| 5,182,779 A | | 1/1993 | D'Agostino et al. | |
| 5,249,251 A | * | 9/1993 | Egalon et al. | ............... 385/123 |
| 5,380,995 A | * | 1/1995 | Udd et al. | ............. 250/227.18 |
| 5,451,772 A | * | 9/1995 | Narendran | ............. 250/227.19 |
| 5,862,273 A | | 1/1999 | Pelletier | |
| 6,233,374 B1 | * | 5/2001 | Ogle et al. | ..................... 385/13 |
| 6,233,746 B1 | * | 5/2001 | Skinner | ................. 250/227.18 |
| 6,590,647 B2 | * | 7/2003 | Stephenson | ................. 356/301 |
| 2002/0040963 A1 | | 4/2002 | Clayton et al. | |
| 2004/0109228 A1 | * | 6/2004 | Aronstam | ................ 359/341.3 |

FOREIGN PATENT DOCUMENTS

GB    2230086 A   * 10/1990   ........... G01K/11/00

* cited by examiner

Primary Examiner—David Bagnell
Assistant Examiner—Shane Bomar
(74) Attorney, Agent, or Firm—Duane Morris LLP

(57) ABSTRACT

A monitoring system and method for monitoring a predetermined set of physical characteristics associated with a structure using the monitoring system. The system is distributed in the structure and comprises a distributed optical sensing device (30), further comprising a fiber optic cable (20, 22); a light source (18a) operatively in communication with the fiber optic cable (20, 22); a light detection device (18b), operatively in communication with the fiber optic cable (20, 22), for measuring the light received at the light detection device (18b) from the fiber optic cable (20, 22); and a data processor (18) capable of using the light measured to calculate a predetermined set of physical parameters describing the predetermined set of physical characteristics.

10 Claims, 3 Drawing Sheets

METHOD AND SYSTEM FOR MONITORING SMART STRUCTURES UTILIZING DISTRIBUTED OPTICAL SENSORS

RELATED APPLICATIONS

The present invention claims priority from U.S. Provisional Application No. 60/214,900 filed Jun. 29, 2000.

BACKGROUND OF THE INVENTION

1. Field of the Invention

The present invention relates to the field of measurement. More specifically, the present invention, in an exemplary embodiment, relates to measurement of selected physical parameters for a predetermined environment using distributed optical sensors. More specifically still, the present invention, in an exemplary embodiment, relates to measurement of temperature, mechanical stress, pressure, vibration and mechanical strain using distributed fiber optic sensors in environments that require distributed measurements over long distances or continuous measurements where individual sensors would be prohibitive due to space constraints and/or costs.

2. Description of the Related Art

Numerous fields require precise measurements of pressure, temperature, and/or strain but prior art methods are either too expensive, too dangerous, and/or too unsuited for use, e.g. due to inference caused or generated by the method. By way of example and not limitation, many prior art sensors are electromechanical and cannot be placed into environments where gasses are volatile or into environments where either other machinery's electromagnetic interference ("EMI") will affect the sensor or the sensor's EMI will affect the other machines.

Using the present invention to provide downhole intelligence may not only allow the industry to collect more accurate reservoir and production data, but may also allow the industry to evaluate, predict, recommend, and take actions downhole without intervention into a wellbore from the surface. For example, the production of unwanted water with oil and gas can have a significant impact on operations and economics over the life of a field. Intelligent systems can improve water separation and reinjection into the downhole environment, thus playing a vital role in water management and offering many new, significant opportunities to reduce lifting and processing costs while producing a substantial positive impact on the environment.

Faster and more accurate decisions are required to improve the performance of the field assets. Integration of a company's expertise and resources to optimize the asset life cycle will require the combination of field acquired data with knowledge management for processing, analysis and proper interpretation of the information.

New processes for drilling, completion, production, hydrocarbon enhancement, and reservoir management have been created by advancements in technology in fields such as high temperature sensing, downhole navigation systems, composite materials, computer processing speed and power, software management, knowledge gathering and processing, communications and power management. Sensor technology, in conjunction with data communications, provides on-demand access to the information necessary to achieve hydrocarbon production levels and costs goals. For example, U.S. Pat. No. 6,192,988 issued to Tubel for "Production Well Telemetry System and Method" describes a downhole production well control system comprising downhole control systems that use short hop transceivers. U.S. Pat. No. 6,192,980 issued to Tubel et al for "Method and Apparatus for the Remote Control and Monitoring of Production Wells" discloses a system adapted for controlling a plurality of production wells is also illustrative.

Fiber optic sensor technology will significantly change the reliability of downhole systems and the ability to place sensors in a wellbore. Distributed optical sensors embedded inside the fiber optic cable will allow the large sections of the well to be monitored instead of a specific zone.

Fiber optic cable and sensor technology will significantly change the reliability of downhole systems and the ability to place sensors in the wellbore. Distributed optical sensors embedded inside the fiber optic cable will allow the entire well to be monitored instead of a specific zone. The cost of monitoring wellbores during production should decrease significantly while the amount of data collected downhole and retrieved and processed at the surface should increase. Fiber optic sensor technology will complement and, in some cases, eliminate production logging runs.

By way of example and not limitation, over the last several decades, new technology development has been fundamental to maintaining the economic attractiveness of developing oil and gas reserves in spite of flat hydrocarbon prices. Monitoring and controlling the processes required to search for and produce hydrocarbons constitutes an ongoing concern in the oil and gas industry. This concern is due in part to the enormous expenses and risks associated with the execution of those processes, as well as environmental and safety factors.

By way of further example and not limitation, methane hydrates are solid, ice-like materials containing molecules of natural gas that represent a potentially significant source of natural gas. The amount of hydrates around the world is estimated to be many times the total amount of natural gas reserves.

The Gulf of Mexico contains a significant amount of methane hydrates in deep water due to the high pressure and low temperature environment conditions. However, these hydrates are not very stable and their dissociation can be slow or explosive depending on the chemical content and concentrations of the hydrates as well as changes in temperature and pressure.

As exploration and production of hydrocarbons continues to move towards deep waters such as in the Gulf of Mexico, hydrate associated seafloor stability issues need to be addressed. Gas hydrate mounds are formed along the intersections of faults with sea floor. The mounds can change significantly in a matter of days. The ability to monitor, evaluate, predict and perhaps control the seabed changes is essential for the safety exploration and production of hydrate natural gas as well as conventional hydrocarbons.

As will be familiar to those of ordinary skill in the fiber optics arts, because the functional properties of fiber sensors include remote operation, immunity to electromagnetic interference (EMI), small size, long term reliability, and capability of responding to a wide variety of measurements, fiber optics is particularly suited for use in high temperature and pressure environments. U.S. Pat. No. 6,233,746 issued to Skinner for "Multiplexed Fiber Optic Transducer for Use in a Well and Method" is illustrative of such fiber optic sensors. U.S. Pat. No. 6,233,374 issued to Ogle et al. for "Mandrel-Wound Fiber Optic Pressure Sensor" is also illustrative.

A large number of techniques using optical fibers for strain measurements have been already proposed. Interferometric methods are almost the only ones providing precision, stability and dynamic ranges which satisfy most of the applications: onboard weighing systems for road vehicles, planes or others; systems dedicated to monitor the integrity of structures; and monitoring of parameters inside the wellbores for oil and gas exploration.

Many methods of obtaining measurements using fiber optics have been proposed in the prior art. As will be familiar to those of ordinary skill in the fiber optic arts, the Raman effect is the appearance of weak lines in the spectrum of light scattered by a substance which has been illuminated by a monochromatic light. The lines occur close to, and on each side of, the main spectral lines, and arise from the inelastic scattering of the photons with atomic or molecular vibrations or rotations in the scattering material. By analogy with the terminology used in fluorescence, the lines corresponding to a loss of energy are called Stokes lines and those corresponding to a gain of energy are called AntiStokes lines.

The frequency difference between the incident photon and the scattered photon gives an energy separation that can be measured. By measuring the energy shift of the scattered photons, the structure of the system can be determined. For example, temperature information related to the system may be obtained by measuring the intensity of the reflected photon at the surface.

Fiber optic gratings system have been proposed for fiber optic sensors that have the potential for use in wellbore applications. The fiber gratings are constructed by doping the core of an optical fiber with material such as germanium. When exposed to light, the index of refraction of the optical core of silica based fiber with appropriate core dopants have been observed to have a modified index of refraction. Use of phase masks or interfering laser beams has been demonstrated to produce multiple variations in the index of refraction along the length of the fiber core producing an internal grating structure. Adjusting the spacing of the period during formation of the fiber grating changes its spectral transmission and reflection characteristics. When a fiber grating is exposed to an environmental effect such as pressure the length of the optical fiber is changed, as is the period of the fiber grating.

For many applications it is necessary to measure both temperature and strain simultaneously. U.S. Pat. No. 5,380,995 to Udd et al. for "Fiber Optic Grating Sensor Systems for Sensing Environmental Effects" describes how using two overlaid fiber gratings at different wavelengths such as 1.3 and 1.5 microns may be used to simultaneously measure two environmental parameters such as strain and temperature at a single point. M. G. Xu, H. Geiger, and J. P. Dakin, in "Multiplexed Point and Stepwise Continuous Fiber Grating Based Sensors: Practical Sensor for Structural Monitoring?", Proceedings of SPIE, volume 2294, p. 6980, 1994, also demonstrated the simultaneous measurement of strain and temperature using 1.3 and 0.85 micron wavelengths and overlaid fiber gratings for point measurements.

In order to make complete measurements of strain internal to a structure it is often necessary to measure all three strain components. There is a continuing need to measure other environmental effects such as transverse strain at a single point and to integrate such fiber grating sensors into practical and economical sensor systems that can be manufactured using available components.

The present system can be used to simultaneously measure and continuously monitor many individual sensors placed along a fiber length. This enables the detection and accurate measurement of both the sensed parameter and environmental effect on each sensor. A normal fiber grating is sensitive to temperature, transverse strain and longitudinal strain effects. Transverse strain effects are particularly important when the fiber sensors are embedded into materials subject to loading such as advanced organic and metallic composite structures. More specifically, some such known sensors use optical fibers in which diffraction gratings have been inscribed, typically known as "Bragg" gratings. The term "Bragg Grating" is used herein below for any diffraction grating, without the field of the present invention being restricted to Bragg Gratings only. By way of example, such sensors are described in U.S. Pat. No. 6,212,306 issued to Cooper et al. for "Method and Device for Time Domain Demultiplexing of Serial Fiber Bragg Grating Sensor Arrays."

As will be understood by those of ordinary skill in the fiber optics measurement arts, a diffraction grating inscribed in the core of an optical fiber is constituted by a succession of periodic changes in the refractive index of the core of the fiber over a given length along the axis of the optical fiber. The cumulative effect of these changes on a light signal transmitted by the fiber is to reflect a significant portion of the signal back towards its injection end. Further, this takes place around a wavelength referred to as the "central" reflection wavelength of the diffraction grating. The central reflection wavelength is a function of the pitch of the grating and of the initial refractive index of the optical fiber core, i.e. its index before the grating was inscribed. For the remainder of the signal, the refraction grating is substantially transparent. Thus, a diffraction grating inscribed in the core of an optical fiber acts like a narrow bandstop filter for the light signal conveyed by the core. U.S. Pat. No. 6,208,776 issued to Pohaska et al. for "Birefringent Fiber Grating Sensor and Detection System" is illustrative of such systems.

In the spectrum reflected from the Bragg grating, this phenomena gives rise to a peak over a range centered on the central reflection wavelength that is relatively narrow thereabout. In the spectrum transmitted through the grating, this also gives rise to a corresponding notch at the said wavelength.

As will be familiar to those of ordinary skill in the optics measurement arts, a Fabry-Perot interferometer includes two semi-reflective mirrors spaced substantially parallel to one another by a given distance so as to define a Fabry-Perot cavity having transmittance or reflectance properties which are affected by a physical parameter. The physical parameter causes the spectral properties of the light signal to vary in response to changes such as pressure. The Fabry-Perot interferometer uses at least one multimode optical fiber for transmitting the light signal into the Fabry-Perot cavity and for collecting at least a portion of the light signal back as a reflected signal at the surface. The sensor is placed in a pressure containing container with a non-intrusive, metal embedded fiber optic pressure sensor. A Fabry-Perot Interferometer is arranged in a terminated, single mode or multi mode fiber to function as a strain gauge. The fiber Fabry-Perot Interferometer (FFPI) is embedded in a metal or other material that isolate the environment from the fiber element part which may be disposed in a wall of the pressure containing container. The metal part and FFPI experience a longitudinal strain in response to the pressure in the container. In another aspect of the invention, a nonintrusive fiber containing the FFPI may be embedded along the axis of a metal housing. The housing may be used to attach a part or structure, which is directly exposed to the pressure, to the wall of the container. Consequently, the housing and FFPI experience a longitudinal strain in response to the pressure on the part or structure. U.S. Pat. No. 6,137,812 issued to Hsu et al. for "Multiple Cavity Fiber Fabry-Perot Lasers" is illustrative.

The need for accurate measurement of parameters is important to the operation of many industries. For example, large vessels such as ocean ships often present hostile environments for electrical sensors, but these large vessels need sensors to provide ongoing, real-time data on stresses present in the vessel structure, e.g. pressure, strain, and the like.

By way of example and not limitation, oil and gas E&P requires precise measurement of exploration data as well as production data. For example, in the hydrocarbon industry the outside of the casing deployed inside of the well is filled with cement. The cement provides a barrier between hydrocarbon producing zones and non-producing zones preventing oil, gas and water from migrating into other geological zones. The condition of the cement is critical in determining the barrier quality. The production of hydrocarbons may also cause the formations to compact, placing a burden on the casing and cement and sometimes causing the casing to fail which creates a potential hazardous condition and causes production to stop. The fiber system of the present invention can be used to monitor for unusual strains or temperature variations that may indicate that the casing is under abnormal strain and/or that fluids may be leaking for one formation to another.

In the prior art, distributed fiber optic sensing cables have been deployed in wellbores to monitor the temperature profile of the well. These fiber optic cables may be inserted into a well such as by pumping it into the well through a ¼" control tube that is assembled along the production tubing.

There is therefore a need for a system and method for signal generation using discrete or distributed acoustic or strain fiber optics sensors embedded or externally attached to a fiber optic cable because fiber optics highly minimizes the risks attendant with electrical sensors in hostile environments. In such systems acoustic information may be used to provide information related to porosity, travel time within the geological formations or other desired statuses of the geological formation during drilling of wells or production of hydrocarbons from the wellbore. The acoustic signals may use a combination of devices to generate or detect the acoustic signals in and out of the wellbore. The signal may be generated using light traveling through a fiber optics medium. The light can generate enough acoustic signals that can be coupled to the medium to be identified. The receivers can be hydrophones, geophones, fiber optics light system, piezo based sensors that can detect the acoustic signal as it travels through the formation, tubing, casing or cement in the wellbore.

Once a well can not produce enough hydrocarbons economically, the well is shut in and abandoned. However, parameters inside the wellbore such as water migration and leaks of fluids or gases from one zone to another have to be monitored. Also, the integrity of the structure has to be monitored to assure that the well structure remains sound. Accordingly, there is a need for a system and method of distribution of individual sensors located throughout a wellbore to monitor subsidence of the formations or wellbore structure after the well has been abandoned or stop producing hydrocarbon or has been shut in.

In the prior art, compressive strength measurements are often taken using what is known as an Ultrasonic Cement Analyzer (UCA). The UCA was developed to measure the compressive strength of a cement slurry as it sets when subjected to simulated oil field temperatures and pressures. Set time and compressive strength are calculated from measured transit time via empirically developed equations. Unfortunately thickening time tests and compressive strength tests do not tell the whole story. Thickening time is a test which only simulates actual job conditions up to the predicted placement time. After allowing for test accuracy variation, a thickening time longer than the placement time allows for some margin of safety but only for continuous pumping at a lower than predicted rate. Thickening time "safety factors" do not directly relate to how long a slurry can remain static and still be moved after an inadvertent or intentional shutdown during placement. With respect to what actually takes place downhole, a thickening time measurement provides information on what happens up to the end of placement time. A thickening time of six hours tells nothing about what change will occur when the slurry is allowed to remain static after pumping. The compressive strength test shows the degree of hydration and set that will occur eight, twelve, or twenty-four hours after placement.

In addition to gas flows through a cement slurry many in the industry are using static gel properties to control the flow of water. Some believe water flows through cement slurries to be the most critical problem encountered while drilling, for example, in deep water in the Gulf of Mexico. Static gel strength development can be quantified and utilized to design slurries that prevent undesirable water flow.

Different measurement systems have heretofore been employed for determining static gel strength. By way of example and not limitation, static gel strength has also been measured by determining the pressure drop across a length of tubing. The basic setup of such an apparatus allows for the circulation of the test slurry through a small diameter tubing. After placement, the slurry is pressurized with water to the test pressure. A sensitive pressure drop transducer measures the pressure drop of the cement as it gels from the entrance to the exit of the tubing. As the cement gels, a corresponding pressure drop will be observed.

The foregoing problems are aggravated in offshore wells which are completed in deep cold water. Such wells include conductor pipes which are cemented from the seafloor or mud line to a depth generally under about two thousand feet below the mud line.

When cementing conductor string casing in the subterranean formation adjacent to the seafloor, the cold temperature of the cement composition after being pumped through the seawater causes the cement composition hydration to be slowed and the transition time to be extended, and as a result, the cement composition often allows the influx of water and other fluids into the annulus. These conditions can lead to cementing job failure, costly remedial work, and increased expense and rig time.

Sensor technology is necessary to evaluate and monitor cement integrity during the hydration process, during the production of hydrocarbons from the wellbore to the surface, and after the well has been abandoned, in part because cement in wells, and particularly the set cement forming the cement sheath in the annulus of high temperature wells, often fails due to shear and compression stress exerted on the set cement. The term "high temperature well" as used herein means a well wherein fluids injected into the well or produced from the well by way of the well bore cause a temperature increase of at least about 100° F. over initial cement setting conditions. The stress referred to herein is defined as the force applied over an area resulting from a strain caused by the incremental change of a body's length or volume When stresses are exerted on the set cement in the well bore, the set cement can fail in the form of radial or circumferential cracking of the cement as well as in the break down of the bonds between the cement and pipe or between the cement and the formation. The failure of the set cement (due to the loss of hydraulic seal of the annulus) can result in lost production, environmental pollution, hazardous rig operations and/or hazardous production operations. The most common hazard is the presence of pressure at the well head in the form trapped gas between casing strings.

Additionally, there is a need for intelligent structures placed as sensors outside the casing to monitor different events that occur during the life of the well. These events may include monitoring of the cement process of the well, subsidence of the formation and settling of the cement in the borehole, monitoring cracks and leaks created in the cement to determine if a cement rework job will be necessary, monitoring corrosion of the casing or tubing monitoring to aid in determining if there will be a potential interface between section of the well that need to stay separate from each other, and measuring formation parameters using acoustic signals, strain or pressure signals generated by sources inside and/or outside the wellbore.

BRIEF DESCRIPTION OF THE DRAWINGS

These and other features, aspects, and advantages of the present invention will become more fully apparent from the following description, appended claims, and accompanying drawings in which:

DETAILED DESCRIPTION OF THE PREFERRED EMBODIMENT

In general, throughout this description, if an item is described as implemented in software, it can equally well be implemented as hardware.

Although the oil and gas industry is used for exemplary reasons herein, the present invention's features and improvements apply to many fields including, by way of example and not limitation, monitoring stress and strain in structures such as nautical vessels 100 (shown in an exemplary representation in FIG. 2), roadways or railroad systems (shown in an exemplary representation in FIG. 5); monitoring stress and strain of structures located undersea, including evaluating methane hydrate stability undersea (shown in an exemplary schematic in FIG. 3 and FIG. 4); monitoring and testing drill stems; external monitoring and testing of wellbore tools such as casing packers, e.g. to insure that the cement was cured properly and the packer is sealing; monitoring reservoirs using pressure, temperature, and flow meters including build up and draw down tests; and monitoring physical parameters of other large structures such as refineries and power generators, including nuclear power plants, by way of example and not limitation including for temperature and strain (not shown in the figures).

Figure 4:
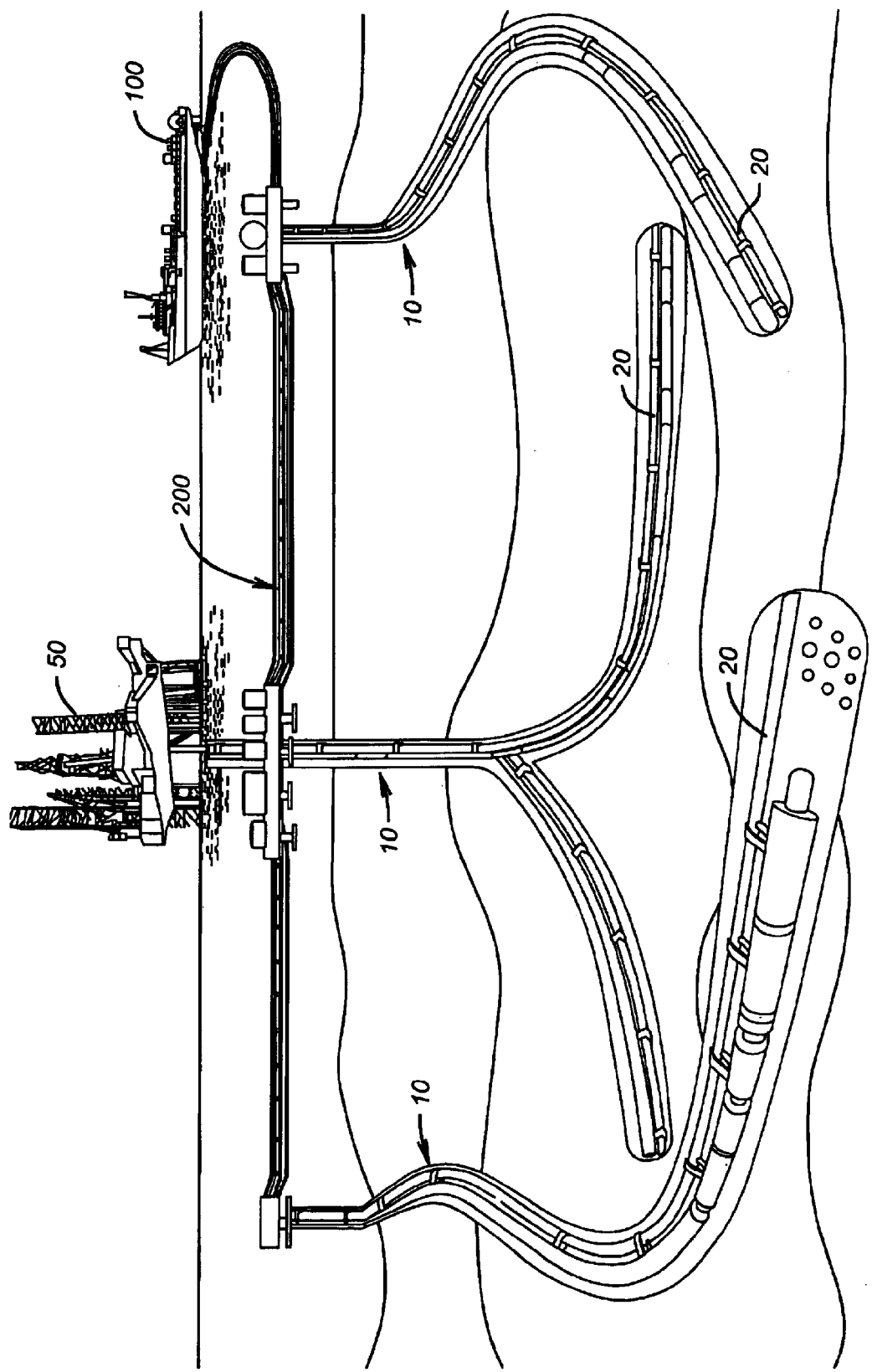
FIG. 4 is a schematic of an exemplary configuration of the present invention for an undersea hydrocarbon system.

As used herein, an "intelligent well" means wells that contain systems that can be controlled remotely from the surface and that provides information constantly from sensors 32 that are deployed in the well permanently. As further used herein, "intelligent completion" means is a system that is composed of sensors and a module that controls the flow of hydrocarbons from the geological formations into the production tubing of the well. An exemplary representation of such intelligent wells is shown in FIG. 4.

Figure 1:
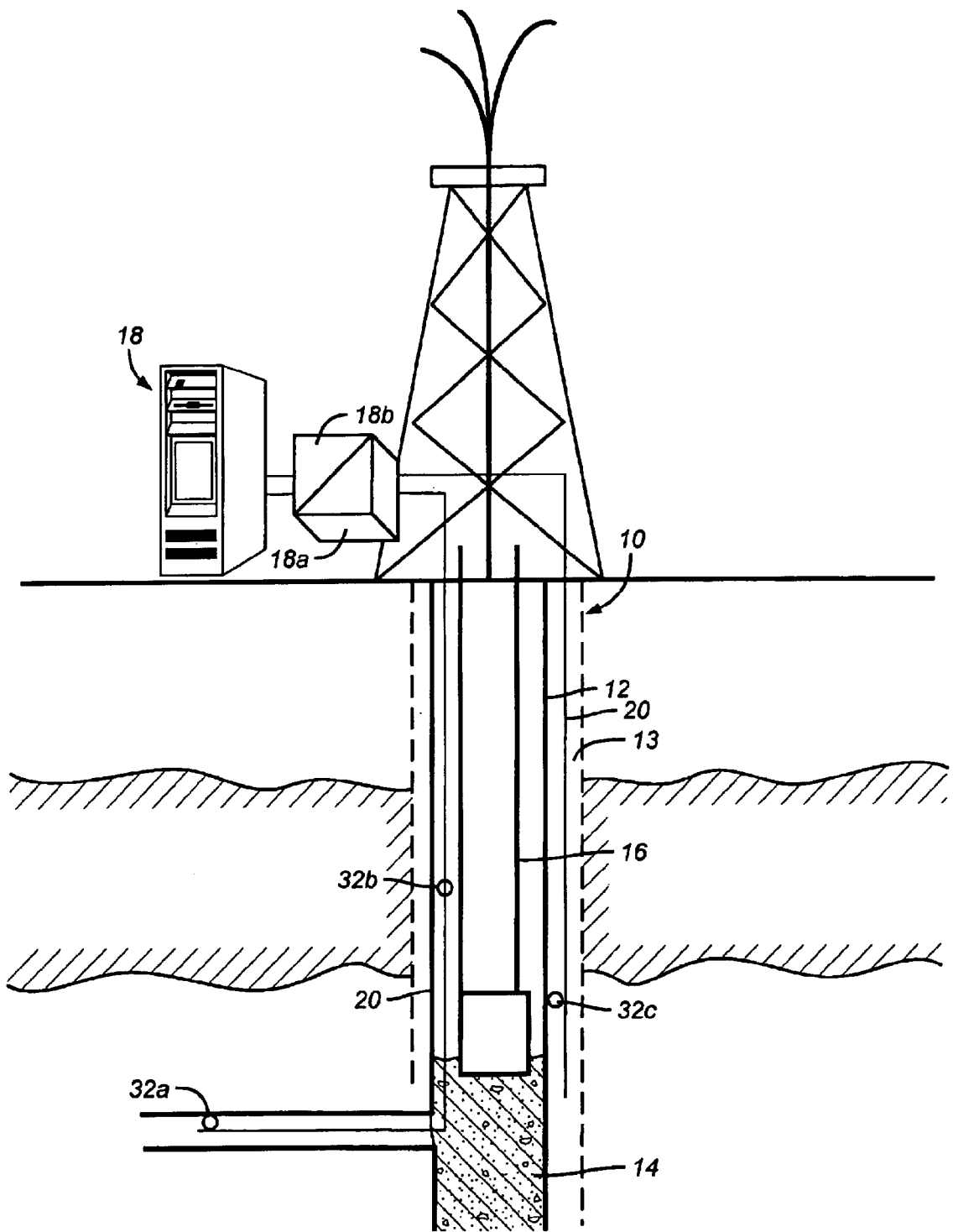
FIG. 1 is a schematic of an exemplary hydrocarbon configuration of the present invention.

Referring now to FIG. 1, a wellbore is shown at 10. Positioned in wellbore 10 is casing 12. Casing 12 is spaced inwardly from the walls of wellbore 10 to provide an annulus space 13 such as for the provision of cement which is shown at 14 and which is being directed through cementing string 16 through the bottom of string 16 and into annulus 13. FIG. 1 shows annulus 13 partially filled and it will be appreciated that eventually annulus 13 will be totally filled with cement 14. In accordance with the teachings of the present invention, a measurement system comprises light source 18a, light detection apparatus 18b, and data processor 18 where data processor 18 may comprise electronic signal processing and/or controller hardware, all of which may be a single unit. The electronic signal processing and/or controller hardware may further comprise a digital signal processor, a phase lock loop, and interface to data processor 18. The measurement system is coupled to one or more distributed optical sensing devices, generally referred to herein by the numeral "30" and comprising fiber optic cables 20, 22, for the purpose of monitoring and evaluating well processes including the cementing process. Fiber optic cables 20, 22 can be either positioned within annulus 13 between casing 12 and wellbore walls, as shown by fiber optic cable 20. Additionally, fiber optic cable can be positioned interior to the casing as shown at 22. Discrete sensors 32 may be associated with the fiber optic cables 20, 22 which may be embedded along wellbore 10 or casing 12 or alternatively may be attached directly to a fiber optic cable 20,22. These sensors 32 may be distributed or single point sensors 32 and may comprise pressure, strength, strain, and/or temperature sensors 32. Examples of suitable sensors 32 and fiber optic sensing systems for use in the present invention are shown in U.S. Pat. Nos. 5,767,411; 5,892,860; 5,986,749; and 6,016,702, all of the contents of which are hereby incorporated herein by reference. It is understood that as used herein and within the claims, the distributed optical sensing device 30 or any sensor 32 may be a fiber optic cable 20, 22 without additional embedded or connected discrete sensors 32.

Light source 18a may comprise a lasing or non-lasing light emitting diode (LED), a white light, or other suitable source. By way of example and not limitation, light source 18a may be a separate unit from data processor 18 or may be integrated into data processor 18. Similarly, light source 18a may be collocated with data processor 18 or operatively connected to data processor 18 such as by wire or wireless methods, all of which will be familiar to those of ordinary skill in the data communications arts. In a preferred embodiment, a software package operating inside data processor 18 may provide graphical interpretation and representation of the data.

The surface system provides for coupling light source 18a to fiber optic cables 20, 22 and detecting signals such as those reflected or created inside wellbore 10 due to well conditions or parameters. By coupling light source 18a into a fiber optic bundle 20, 22 or into individual optical fiber optic cables 20, 22, light may be transferred to optical sensors 32 located in a remote location. Sensors 32 may further be coupled to guiding means such as a tube disposed in a wellbore.

Optical sensors 32 may be adapted to modulate light in response to various stimuli. As preferably embodied herein, these optical sensors 32 are designed to sense pressure, temperature, and/or strain in the structure. Furthermore, optical sensors 32 may be adapted to modulate the light in different ways so as to encode multiple signals. For example, strain may be encoded by intensity, pressure by frequency and temperature by phase of the optical signal.

In a preferred embodiment, optical sensors 32 may be interferometric sensors illuminated by a broad band light source. By way of example and not limitation, multiple light spectra may be used, each comprising a series of peals wherein the peak spacing may be processed to quantify stimuli such as pressure or temperature. Reflected light would brought back to the input of light detection device 18b such as an imaging spectrometer (not shown in the figures), or to data processor 18. The light from each fiber optic cable 20,22 may be collimated and presented incident to a diffraction grating. Diffracted light may then be imaged onto a light sensor such as a line of a CCD array (not shown in the figures) so that by reading out that line the resulting spectrum can be obtained. In a preferred embodiment, each return fiber 20, 22 may produce light in a different spectrum or to a different line of the CCD array, allowing multiple spectra to be recovered for processing.

As used herein, an intelligent or smart structure is a structure that has distributed optical sensing devices 30 embedded into it. Embedding these distributed optical sensing devices 30 into a structure allows the structure to provide information such as its health status and aid in the determination of whether the structure is under unusual or unacceptable strain, stress, and/or temperature influences. For example, a bridge that has embedded distributed optical sensing devices 30 can provide information on its joints and stress points, e.g. if those joints and stress points are in good condition or if work is required to maintain the bridge.

Distributed optical sensing devices 30 can achieve improvements over electromechanically based systems in the areas of capability, cost effectiveness, reliability, and suitability for a particular environment, e.g. placement in volatile, gaseous areas. These improvements can lead to reductions in development costs, lower operating costs, and higher efficiencies, e.g. greater hydrocarbon recovery in the field of oil and gas exploration and production.

Strain sensors using optical fiber optic cable 20,22 have evolved in almost all the fields involving strain sensing measurements of mechanical microdeformations. In addition to traditional applications which are presently carried out by strain gages of resistive, piezoelectric or other types, strain sensors such as distributed optical sensing devices 30 using optical fiber optic cables 20,22, due to their small size, can be integrated within the structures to be monitored.

The properties inherent to optical fibers or devices can overcome numerous drawbacks of prior art sensors. For instance, distributed optical sensing devices 30 using optical fibers are immune to electromagnetic fields, provide better precision than traditional gauges, and provide resistance to harsh environment conditions.

In the oil and gas industry, real-time online measurement and monitoring of some key borehole parameters are significant for the optimization of the downhole production process. Some of the potential applications of fiber optics in the oil field include:

Monitoring well temperature with real-time distributed optical sensing devices 30 to manage steam floods in heavy oil reservoirs, detect inflows in horizontal wells, and optimize the performance of electrical submersible and progressive cavity pumps;

Measuring downhole pressure to provide data for better, faster reservoir characterization and improved forecast of reservoir capability;

Measuring oil flow at various critical locations in a reservoir to provide important information about reservoir architecture, geometrical dimensions, zonal performance, and well-to-well interactions, further contributing to reservoir optimization and reserve recoveries;

Controlling downhole flow control devices to modulate the production of hydrocarbons from the geological formations into the production tubing for intelligent completion applications; and Enabling highspeed communication interfaces between surface systems and downhole tools.

It is currently anticipated that systems of the present invention may comprise distributed temperature measurement and monitoring capabilities to provide a profile of wellbore 10 based on temperature measurements at predetermined distances along the main axis of wellbore 10, in the preferred embodiment with a precision of as close as one meter. This may be accomplished as described herein below by using fiber optic cables 20,22 as sensors 32 along with or in place of discrete sensors 32. By way of example and not limitation, in this manner, the present invention may provide monitoring of steam and water flood operations in injector wells to determine where the fluid injected is being deployed in the formation. The present invention may be used to optimize injection and to increase the production of hydrocarbons. The present invention may further provide for monitoring of hydrocarbon entry into wellbore 10, e.g. where the hydrocarbons and water are being produced from within wellbore 10. Such information may held an operator evaluate production and shut in zones producing water. In further embodiments, the present invention may provide for monitoring of the performance of artificial lift systems to extend the life of the systems and to optimize production. Optimization of gas lift processes may also provide indications of gas entry into wellbore 10 from injection systems at the surface.

In a further embodiment, a single point pressure system may be used to provide the ability to monitor production and perform reservoir testing and evaluation. Such an embodiment may further allow an operator to monitor the reservoir such as by monitoring pressure drawdown levels and determine its size based on build up tests. Such an embodiment may further allow an operator to monitor pressures for equalization of production pressures among multiple zones where multiple zones are produced simultaneously.

Distributed optical sensing devices 30 of the present invention can measure environmental parameters to high accuracy with technologies that are lightweight, insensitive to electromagnetic interference, and capable of withstanding extreme conditions including wide temperature variations, large shocks and vibration, and corrosion.

One method to be used with distributed optical sensing devices 30 of the present invention is the Brillouin scattering method which uses scattered light that occurs from an interaction between an incident light and an acoustic wave generated by the incident light in an optical fiber. The scattered light frequency is shifted from the incident light frequency by an amount determined by the material. This frequency is called the Brillouin frequency shift. The frequency shift is proportional to the strain and temperature affecting the fiber material. The Brillouin scattering technique can be used to measure strain and temperature at distances of tens of miles from the source panel. A further technique using a time domain reflectometer may be used to determine the location where the temperature and strain measurements were made in the fiber optic cable 20,22 providing a distance of the measurements from light source 118*a*.

Distributed optical sensing devices 30 system of the present invention differ from prior art point sensor systems in that the present invention may use fiber optic cable 20, 22 itself as the distributed optical sensing device 30. Once fiber optic cable 20, 22 is attached to a structure, strain and temperature measurements may be taken at any and every point along fiber optic cable 20, 22, a length that could extend tens of thousands of meters.

Several types of light scattering can occur as light is transmitted through an optical fiber. In general, scattering takes place when light passes through a non-homogeneous medium and a fraction of that light is reflected by the discontinuities in the medium. In an optical fiber, discontinuities can arise from several sources including large scale manufacturing defects and localized changes in the chemical composition of the fiber. Each type of discontinuity causes a different type of scattering process to occur. By way of example and not limitation, Rayleigh scattering is caused by small variations in the refractive index of the glass that are frozen into the fiber optic cable when it is fabricated.

Compression and rarefaction of the glass in fiber optic cable 20, 22 due to longitudinal elastic waves may cause localized changes in the refractive index of the fiber. Brillouin scattering occurs when the light is scattered by acoustic waves, called phonos, caused by lattice vibrations. Since the phonos travel at approximately 6000 m/sec, light in fiber optic cable 20,22 is Doppler shifted in frequency when it is Brillouin scattered. The frequency difference between the incident wave and scattered light is referred to as the Brillouin shift and can be calculated by the relationship $$V_b = (2nv_a)\lambda$$

where $V_b$ is the Brillouin shift, n is the refractive index of the fiber, $v_a$ is the acoustic velocity of the fiber, and $\lambda$ is the wavelength of the incident light beam. For a given fiber under constant environmental conditions, the Brillouin shift is also constant for any given incident light wavelength.

The Brillouin shift may be used as the basis for the scattering light to be used in distributed optical sensing devices 30. The Brillouin shift of a fiber is directly related to the index of refraction of the fiber and the acoustic velocity. These parameters change in response to environmental conditions of the fiber such as temperature and strain. Lattice vibrations in motion in the fiber induce a Doppler shift in the scattered (Stokes) light. The Stokes frequency is downshifted by the Brillouin frequency. The Brillouin frequency is related to the temperature and strain conditions of the fiber and by using pulses of laser light to interrogate the fiber, the Stokes light can be analyzed as a function of time, or equivalent distance along the fiber allowing distributed measurements to be made. The interval between measurements has been reduced recently due to on going research from about five meters which is not quite good enough for most applications to approximately fifty centimeters that addresses the requirements in most applications. The strain and temperature may be measured by analyzing the Brillouin loss spectrum of the sensing fiber in the time domain. The Brillouin frequency is determined by finding the center frequency of the Brillouin loss spectrum. As the accuracy of this determination drops with either a reduction in signal to noise ratio or an increase in line width, these two affects cause deterioration in the resolution of the Brillouin frequency. This has the effect of reducing the strain or temperature resolution as one improves the spatial resolution. If one also considers the loss of signal that is a result of increasing the overall fiber length, then there is a three-way trade off between spatial and strain resolution and total sensing length.

In a preferred embodiment, a data acquisition panel may be present. The panel comprises two lasers that are either located at opposite ends of fiber optic cable 20,22 or combined on a single end of fiber optic cable 20, 22. These lasers are used as continuous light pump and a pulsed light probe beam. In the preferred embodiment, a preferred method uses the Brillouin loss to calculated desired parameter measurements by measuring power drop of the continuous wave pump signal as the pulsed and continuous lights interact in fiber optic cable 20, 22. Measurement methods may comprise stepping the frequency difference of the lasers through a range of frequencies around the anticipated Brillouin frequency. The power loss is measured at each frequency and the Brillouin shift is determined by the frequency where the highest power loss is encountered and hence the fiber strain or temperature measurement is determined by the relationship between the power loss and the temperature and strain. The Brillouin frequency can be expressed by the equations related to power loss and frequency shift as following:

$$V_b = V_{b0} + (dV/dT)T + (dV/dE)E$$

$$P_b = P_0 + (dP/dT)T + (dP/dE)E$$

where $V_{b0}$ is the Brillouin frequency at a temperature (T) of 0° Celsius and a strain (E) of 0•strain and $P_0$ is the Brillouin power at 0° Celsius and a strain (E) of 0•strain. The parameters (dV/dT) and (dV/dE) are the Brillouin frequency change with temperature and strain respectively.

These two equations can be used in combination to obtain both the strain and temperature exerted onto the cable using a single fiber. The addition of a high speed Optical Time Domain Reflectometer (OTDR) may provide the capability of measuring the location where the Brillouin scattering occurred throughout fiber optic cable 20, 22. The use of a single fiber optic cable 20 to measure multiple parameters can reduce the system cost and increase its reliability.

Once a well cannot produce enough hydrocarbons economically, the well is shut in and abandoned. Distribution of individual sensors 32 located throughout wellbore 10 may be used to monitor subsidence of the formations or wellbore 10 after the well has been abandoned, stop producing hydrocarbon, or has been shut in. Parameters inside wellbore 10 such as water migration and leaks of fluids or gases from one zone to another have to be monitored. Additionally, conditions of wellbore 10 and geologic structures through which wellbore 10 passes may be monitored, by way of example and not limitation comprising geological formation porosity and permeability and cross-well tomography along with acoustic phenomena impinging on one or more structures inside the wellbore including wellbore 10 itself.

The integrity of the structure also has to be monitored to assure that the well structure is sound. For example, subsidence created by erosion of the formation and/or removal of hydrocarbons and water from inside wellbore 10 may cause stresses in the cement barriers in wellbore 10 causing cracks and leaks to occur. These anomalies in cement 14 may cause movements of fluids in wellbore 10 from one zone to another. The ability to have permanent sensors 32 in wellbore 10, either as discrete sensors 32 or by using fiber optic cable 20,22 that can monitor the cracking or leaks in wellbore 10 will allow the operator to perform a rework to repair the problems before a failure occurs. Monitoring corrosion of casing 12 or tubing 16 may additionally help determine if there will be a potential interface between sections of the well that need to stay separate from each other.

Acoustic signals, strain or pressure signals generated by sources inside and/or outside the wellbore that can be used to measure formation parameters. By way of example and not limitation, optical sensors 32 or conventional sensors 32 can be deployed on the outside of casing 12 and embedded in cement 14 for monitoring signals traveling throughout the geological formations. These signals can carry information related to fluid content in the formation, geological formation structure, water front, subsidence of the formation and water movement behind pipe and throughout the formation. Optics sensors 32 can be deployed inside or outside of casing 12 and inside or outside of the production tubing. A source of acoustic signal such as fluid flow during production, light traveling through a fiber optics cable 20,22, or a remote source of energy can generate the signals that will travel through the formation to provide formation parameters. The source of acoustic energy can be deployed in the wellbore permanently or having the capability of being retrievable for high resolution and local area applications. The receivers can also be a discrete system based on piezoelectric, geophones, hydrophones or the new fiber optics strain sensors 32. Strain sensors 32 using fiber optics can be Bragg Gratings as well as Fabry-Perot or any other sensor 32 technique where light is used and its characteristics modified by the acoustic or pressure signal created by a natural or man-made source. A distributed system of the present invention may comprise a surface system capable of transmitting light into wellbore 10 via a fiber optic cable 20,22 wherein the same system will be capable of detecting, decoding and processing the light reflected from inside wellbore 10 as the light travels through fiber optic cable 20,22. The acoustic information can also be used to generate information related to cement health in the outside of casing, such as bonding to the formation and casing and cracks.

The present invention may also be used for as a seismic system for formation and fluid content mapping. The ability of detecting and measuring the scattered photons as the light travels through fiber optic cables 20,22 for strain and temperature allows for the measuring of seismic information at the seabed 200 or inside the wellbore 10. Fiber optic cable 20,22 can be deployed permanently or temporary in the wellbore 10 or seabed 200 or on land. The present invention can "listen" to production noise generated by fluid flow by detecting photon changes caused by noise. Additionally, the present invention can detect strain created by a source located inside or outside wellbore 10. Distributed optical sensor 30 may be deployed in the cement outside or inside casing 12 or inside tubing. If the source is located in a nearby well, distributed optical sensor 30 can be used to gather high resolution information for the evaluation of the formation and the fluids traveling through those formations. This method is known in the art as cross well tomography.

Using optical sensors 32, pressure, temperature, strain, and acoustic parameters may be measured and calculated to help assure that the well is being monitored properly. The use of distributed temperature and strain techniques related to Rayleigh, Raman and other reflection and photon scattering techniques can provide a significant advantage over electromechanical sensors 32. In a preferred embodiment, the entire well may be monitored using a single fiber optic cable such as fiber optic cable 20 instead of deploying multiple sensors 32 in the well. This improves reliability.

Figure 2:
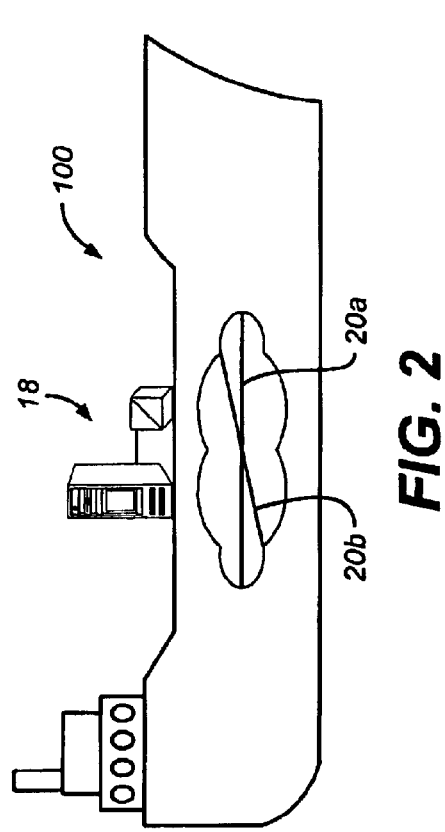
FIG. 2 is a perspective plan with a partial cutaway of an exemplary vessel configuration of the present invention.

Referring now to FIG. 2, for use in nautical vessels 100 such as an ocean liner, an oil tanker, or a Navy vessel, the distributed optical sensing technology of the present invention can be used to monitor the strain on vessel walls and monitor for fire throughout the entire ship. The distributed optical sensing technology of the present invention allows for complete monitoring of the ship such as to provide early warning of potential problems, to prevent accidents, and to determine maintenance schedules. As used herein, "vessel" means a nautical structure used for locomotion in or on water such as a boat, ship, tanker, or the like.

Additionally, vessels 100 may contain tanks containing fluids, such as hydrocarbon-based fluids such oil or refined product, water, edible oils, and the like. The distributed optical sensing technology of the present invention allows for monitoring of levels of the fluids to provide early warning of potential problems with the tanks as well as to prevent accidents and to determine maintenance schedules.

Sensitive structures may also be implemented according to the teachings of the present invention. By way of example and not limitation, prior art vessels 100 such as military and commercial sea vessels 100 may contain hundreds if not thousands of sensors 32. Many of these sensors 32 are used to provide measurement points in hostile environments and may be based on electromechanical processes. These sensors 32 are prone to EMI, low reliability, and high cost. Additionally, these sensors 32 may present sparking or other phenomena which makes shielding them extremely important and/or their suitability for use in particular environment questionable. However, optical sensors 32 are immune to most of the EMI and other hazardous environmental problems, ameliorating shielding and further reducing weight, cost, and complexity. Additionally, the weight of electrical cables required to connect non-optical sensors 32 adds to the overall weight, cost, and complexity of vessel 100.

In a currently envisioned embodiment, the implementation of a distributed strain and temperature system in vessel 100 may additionally have a positive impact the design and production of ships by aiding greater flexibility with the design and continuous monitoring during operation of the vessel 100. The system of the present invention may further provide operators with more complete access in real time to information related to the health of vessel 100 as a complete system and allow operators to be able to more rapidly detect potential problems related to the operation of vessel 100.

Discrete optical sensors 32 may be used to obtain temperature, strain, and pressure measurements in virtually every area of vessel 100. In an embodiment of the present invention, a single fiber optic cable 20 (or a series of redundant fiber optic cables) may be used to interconnect numerous optical sensors 32, lessening weight, complexity, and cost. In the preferred embodiment, a single fiber optic cable such as fiber optic cable 20a may be used in place of using discrete sensors 32. Larger ships may have a single system of fiber optic cables 20 such as on a per deck basis. Additionally, a distributed optical sensing device 30 in vessel 100 may further comprise at least one optical fiber 20b that at least substantially horizontally stretches along an interior perimeter of vessel's 100 hull via the bow. Vessel 100 may also have at least one optical fiber 20a that at least substantially horizontally stretches along an interior perimeter of vessel's 100 hull via the stern.

Using techniques as described herein such as photon scattering, strain loads and temperature monitoring may be obtained for the entire vessel 100 as opposed to sets of discrete points. The techniques may include spontaneous anti-Stokes Raman photon backscattering waves, which is modulated by temperature, and spontaneous Rayleigh backscattering waves, modulated by the strain and pressure and Brillouin scattering.

In the currently envisioned preferred embodiment for vessels 100, the Brillouin technology is the system of choice for temperature, strain and pressure measurements. In this system, temperature, strain and pressure measurements are obtained by in time by demodulation. The position of the local domain is determined by time interval, known as optical time domain reflection (OTDR). The system can be used for long distance measurements as when the laser pulse couple into the optical fiber the excited photons transmitted in optical fiber collide with the molecules of the optical fiber. During the time that the excited photons come into collision with the molecules, the scattering photons are generated, including Rayleigh scattering photons (elastic collision); Brillouin scattering photons and Raman scattering photons (non-elastic collision).

Figure 3:
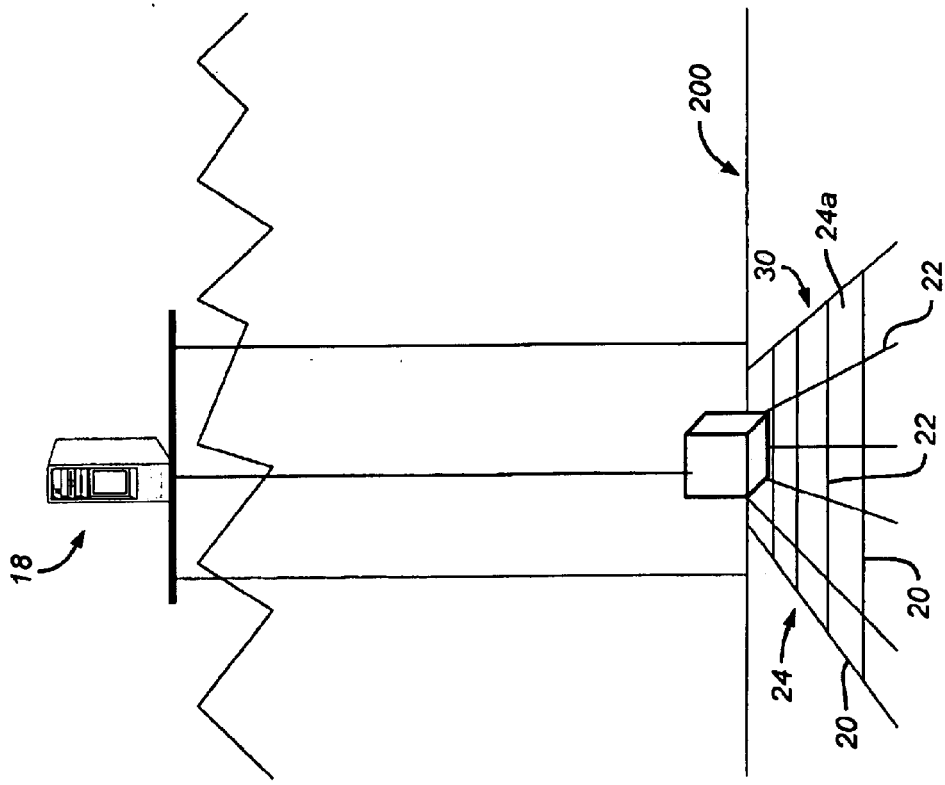
FIG. 3 is a schematic of an exemplary methane hydrate grid configuration of the present invention.

Referring now to FIG. 3, for use undersea of the present invention, the first step in the development of the distributed optical sensing device 30 system of the present invention using Brillouin photon scattering techniques is to identify the requirements for seabed and wellbore deployment. By analyzing the implementation of existing sensors 32 and requirements for sensing parameters, it is possible to develop a system that addresses the necessities required for real-time strain and temperature monitoring, e.g. for methane hydrate evaluation. Seabed 200 requirements may be evaluated for the ability to install a continuous fiber optic cable 20 throughout the seabed zone of interest.

The following exemplary embodiments are illustrative of the present invention's systems and methods but are not limitations on the present invention which is limited by the inventions claimed herein.

Referring again to FIG. 1, in a further exemplary embodiment, the present invention may be used with oil and gas exploration and production. By way of example and not limitation during the construction of oil and gas wells a bore is drilled into the earth. Casing is then lowered down the bore. It is known in the art of well cementing to position a sheath of hardened cement in the annular space between a well pipe, such as a casing, and the walls of a wellbore which penetrates a subterranean formation. The process of cementing is well known in the art. U.S. Pat. No. 6,173,783 issued to Abbott-Brown, et al. for "Method of completing and producing hydrocarbons in a well" is illustrative.

The sheath supports casing 12 in wellbore 10 and prevents undesirable movement of formation fluids such as oil, gas, and water within annular space 13 between subsurface formations and/or to the surface of the earth. It is also well known that the process of positioning the sheath is referred to as primary cementing.

During primary cementing, a slurry of hydraulic cement in water is formed and the slurry is pumped down casing 12 and circulated up from the bottom thereof in annulus 13 to a desired location therein. The slurry is then permitted to remain undisturbed in annulus 13 for a time sufficient to enable the hydraulic cement to react with the water in the slurry, i.e., to set and thereby position the sheath of hardened cement.

Cementing operations are conventionally performed with slurry formulations based on hydraulic cement and completed with other additives. It is well known that high temperature and high pressure conditions are very difficult for the success of cementing operations because notably the rheology of such slurries is difficult to control or adjustment of the setting time is very delicate.

The basic design of a cement slurry starts with determining what general properties are needed for predicted well conditions. With the basic slurry formulation established, two physical properties of the slurry are of initial concern. The cement must remain fluid long enough to be pumped to its desired location downhole. Then, once the cement is in place it must set and develop an adequate compressive strength value within a specific time period.

Another innovative area for the present invention is the ability to place distributed optical sensing devices 30, such as sensor 32b, either inside or outside casing 12 to monitor different events that occur during the life of the well, including monitoring the cementing process and cement status of the well. Cement evaluation is one of the areas in the oil business that has not evolved to a point where the measurements are accurate. For example, available sensors 32 such as acoustic well logging tools can only detect less than one inch into the cement from the casing.

The present invention's sensors 32 may further be embedded in or attached to a fiber optics cable such as 20 which is deployed inside the wellbore but outside a casing string 12 such as sensor 32a or sensor 32c. In alternative embodiments, the present invention's sensors 32 may also be embedded or attached to a fiber optics cable such as 22 which is deployed inside the casing along the longitudinal axis of the wellbore.

Distributed or single point pressure, strain, and/or temperature sensors 32 of the present invention can be deployed in the well inside or outside of the casing such as sensor 32b before the cement process starts. The present invention's sensors 32 may then be used to monitor the cement curing process as the cement is pumped into the wellbore. The ability to determine cement cracks and bonding of the cement to the casing and formation is critical to the proper isolation of hydrocarbon producing zones from other zones such as fresh water areas. The real time or delay monitoring of the data generated in the wellbore will provide significant information that will allow the operator to correct problems related to the cementing process of the wellbore.

The cement during curing generates heat that can be detected by a distributed temperature system. The heat dissipation can be affected by the coupling of the cement to the formation and/or casing. Hence, the temperature signature of the cement curing process will be dependent on the bonding of the cement to the formation and/or casing.

A fiber optics cable that has a light signal traveling through it can also be used to detect acoustic signals traveling through the cement. As noted above, sensors 32 may also be placed on the inside of casing 12 and acoustic signals generated by the light traveling though fiber optic cable 22 may be used as the source for the acoustic signal that will travel through the cement to evaluate the cement strength.

In a preferred embodiment, fiber optics cables 20, 22 have no associated discrete sensors 32. Instead, the fiber optics cable itself is used to acquire the necessary information using Raman and/or Rayleigh and/or Brillouin techniques wherein reflected photons are monitored from the surface and utilized. The advantage of this latter embodiment over the use of single point or distributed downhole sensors 32 (such as the Bragg grating sensors 32 described in the aforementioned patents) is improved reliability, lower cost as well as more precise measurements.

In addition, the foregoing techniques for monitoring and evaluating a cementing process finds practical applicability not only for wellbores, but also in construction and other areas where cementing (particularly downhole cementing) is needed. For example, this fiber optic monitoring process may be used for monitoring the cementing of pylons, steel beams, support structure, and the like for bridges and buildings.

Operators of wellbores need to be able to determine the characteristics of the reservoir upon the perforation of the well to start production. The fiber optics system of the present invention can be deployed in the wellbore along a drill-stem test ("DST") work string and provide pressure and temperature readings throughout the perforated zones.

Referring now to FIG. 4, the present invention may be used with production platforms located offshore 50, drilling rigs located offshore, production platforms located onshore, and drilling rigs located onshore. For these uses, the present invention may utilize fiber optic cable 20, which may comprise single fiber optic cable and multiple fiber optic cable, as the distributed optical sensing device 30. In additionally contemplated embodiments, the present invention may further comprise single point and distributed sensors 32 operatively connected to the fiber optic cable at predetermined locations along the fiber optic cable. The distributed optical sensing device 30 can then be placed throughout multiple axes of the structure and the health of the structure can be monitored continuously or on demand.

The use and integration of new technologies for optimized reservoir management and improved recovery of hydrocarbons including 4D seismic surveys, closed-loop drilling, intelligent completions, downhole oil water separation, reservoir modeling, and knowledge management technology, may help create more productive wellbores 10, in less time, with fewer environmental risks. These intelligent systems, as exemplified in FIG. 4 for an offshore reservoir, will require flexibility to adapt to the many complex reservoir requirements and harsh environments, including ultra deepwater drilling, completions, and production; subsea exploration; heavy oil production environments; and multizone production commingling. Intelligent well technologies utilizing the present invention may further be used with in situ power such as generation learning machines, hydrocarbon projects, processing management, and planning.

Referring now to FIG. 3 and FIG. 4, in a further embodiment, the present invention may be utilized to develop an understanding of hydrate systems in near sea floor sediments as well as sedimentary processes, including sedimentary mass movement and methane release, to allow development and deployment of safe, standardized procedures for ocean based hydrocarbon production.

Fiber optic cables 20 may be placed on sea floor 200 as well as deployed inside wellbore 10 to provide continuous, real-time monitoring of strain and temperature parameters over distances of up to fifty kilometers with resolution of up to one meter. Use of a single fiber optic cable 20 may provide measurement points equivalent to having hundreds of thousands of discrete sensors deployed along the single fiber optic cable 20. Multiple fiber optic cables 20 may be deployed within a grid pattern such as grid 24 on seabed 200. Fiber optic cable 20 may also be located outside casing 12 in wellbore 10 to monitor forces exerted on the entire casing 12 due to hydrate shifts to provide a better understanding of the requirements for casing design and deployment in hydrate bearing zones.

The ability to monitor strain and temperature of the seabed over extended lengths (around fifty kilometers per fiber optic cable 20) may be used to obtain information on the stability of seabed 200 that can not be obtained with discrete sensor technology. The fiber optic distributed system of the present invention may allow the creation of grids 24 of data acquisition fibers 20 located in areas rich in methane hydrates to monitor an entire area. Three dimensional graphs may be provided in real time to display the data in a way that can easily understood such that problems with instability within seabed 200 or wellbore 10 may be detected almost immediately.

In a currently envisioned embodiment, resolution of fiber optic cable 20 may be changed such as by a "zoom in" feature to allow an operator to focus on individual areas of grid 24 being monitored, e.g. area 24a.

Existing commercial fiber optics sensor technology requires that discrete sensors 32 be manufactured and attached to fiber optic cables 20 or embedded into fiber optic cables 20. These existing discrete technologies have limited number of sensors 32 that can be attached to fiber optic cables 20 due to light losses and decreases of the strength of fiber optic cable 20. The present invention, using methods such as distributed Brillouin photons scattering, allows for the acquisition of information throughout the entire length of fiber optic cables 20 deployed within wellbore 10 and seabed 200 without the need for discrete sensors 32 attached or embedded onto fiber optic cables 20. Additionally, the present invention system may further provide a log of well/seabed conditions during their operation that will simplify the evaluation of the stability of methane hydrates and determination of potential problems before they occur.

The identification of critical and non critical parameters and locations to be monitored on the seabed will provide the requirements for strain and temperature data processing and data transfer for proper resolution and sensitivity of the data acquired. By determining the critical areas for monitoring the processing panel can give priority to the information acquired in the critical areas of the seabed and update the information faster and more often than the information from non critical areas. These techniques will optimize the data acquisition, processing and storage as well as optimize the Brillouin technique for spatial resolution and accuracy of the data.

The data acquisition panel will have to withstand harsh environments including high shock and vibration. The data acquisition and processing panel requirements will be determined during the first phase of the project. The specifications of the panel will be dependent on the sensor requirements. The update rate of the sensors 32 will determine the storage and data transfer capabilities of the system. The higher the sample rate the more data will be stored and transferred to a data storage device.

The first step in the development of a distributed sensing system using Brillouin photon scattering techniques is to identify the requirements for seabed and wellbore deployment. By analyzing the implementation of existing sensors 32 and requirements for sensing parameters, it is possible to develop a system that addresses the necessities for the methane hydrate evaluation for real time strain and temperature monitoring. The entire well and seabed requirements will be evaluated for the ability to install a continuous fiber optic cable throughout the entire well and seabed zone of interest. The identification of critical and non critical parameters and locations to be monitored on the seabed will provide the requirements for strain and temperature data processing and data transfer for proper resolution and sensitivity of the data acquired. By determining the critical areas for monitoring the processing panel can give priority to the information acquired in the critical areas of the seabed and update the information faster and more often than the information from non critical areas.

The fiber optic cable required for the monitoring of strain and temperature is unique to the application where it is deployed. In seabed monitoring applications, a significant amount of attention will be given to the strength and reliability of the fiber housing used for the protection of the fiber in harsh environments. There may also be requirements for different cables and fibers for different applications such as seabed or donwhole. The data acquisition and processing panel will be based on a single point connection to the fiber to obtain the strain and temperature parameters. The laser strength will be based on the length of the fiber required for seabed monitoring. The resolution and update speed of the surface panel will determine the storage and data transfer capabilities of the system. The evaluation of the location of the surface panel on the platform will dictate the requirements for explosion proof and intrinsically safe designs.

The fiber optics cable may utilize a new technology that uses unique fiber coating to eliminate hydrogen migration that causes fiber failures in harsh environment such as in refineries, traditional power generation facilities, and nuclear power generation facilities. By way of example and not limitation, fiber optics cables 20, 22 may utilize a fiber coating to eliminate hydrogen migration that causes fiber failures in harsh environment. One cable development technique current envisioned encapsulates fibers in fiber optic cable 20,22 in a metal tube for high pressure and high temperature and for protection against crushing. A non-compressible material may further be used to fill the space between the fiber and the inner wall of tubing such as stainless steel tubing. In such an embodiment, fiber optic cable 20,22 may comprise a jacket suitable to protect the fiber optic cable 20,22 along a predetermined portion of its length. The jacket may comprise metal and composites. Additionally, fiber in the fiber optic cable 20,22 may be manufactured using no phosphorous to eliminate hydrogen and hydroxyl migration that can attack and destroy the fiber.

Figure 5:
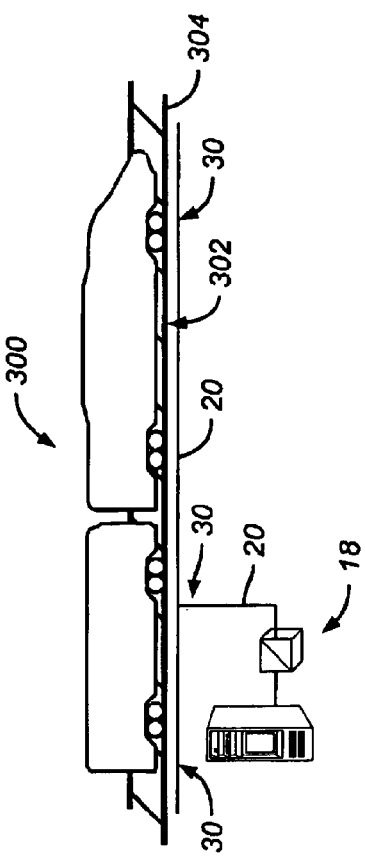
FIG. 5 is a schematic of an exemplary configuration of the present invention for a railway system.

Referring now to FIG. 5, the transportation industry also has requirements for intelligent structures. By way of example and not limitation, the present invention may be used for monitoring of the process of construction of a highway or rail system (shown in the figure as rail system 300). The present invention may be used to determine stress, strain, pressure, temperature, vibration and other parameters that are exerted on the structure during the construction of the structure, e.g. the road bed or rail bed 302. Distributed fiber sensing device 30 may be embedded in the structure or placed on the outside of the structure, e.g. a rail 304, to monitor the structure and help assure compliance with manufacturing requirements. By way of example and not limitation, distributed fiber sensing device 30 can determine if there is a problem with the rail system that could cause the train to derail. The ability to monitor strain along the axis of a fiber optic cable 20 associated with distributed fiber sensing device 30 provides this unique capability. Further, the ability of Brillouin technology to monitor events occurring along distributed fiber sensing device 30 may provide a resolution of ten centimeters or better, thus allowing for accurate measurement of the entire length of fiber optic cable 20 instead of discrete points in fiber optic cable 20.

Using rail system 302 as an example, the present invention may be used to determine a train's location in the system monitored by distributed fiber sensing device 30 because the train will cause a strain in rails 304 as well as vibration that can be detected by distributed fiber sensing device 30. Further, the present invention may be used to monitor wear of rail system 302 (or bridge or road) due to the traffic on the structure. By way of example and not limitation, the present invention can detect the stress and strain on rails 304 using distributed Rayleigh, Brillouin, or Raman scattering techniques or other techniques used to obtain information as the light reflects as it travels in and out of fiber optic cable 20. In this manner, distributed fiber sensing device 30 and discrete sensors 32 located throughout rail system 302 or road system may also be used to monitor other adverse conditions such as subsidence of the ground that can damage the structure. The use of distributed fiber sensing device 30 to detect and measure physical parameters such as pressure, temperature, strain, and acoustics can assure that the structure is being monitored properly.

The use of distributed temperature and strain techniques related to Rayleigh, Brillouin, and Raman and other reflection and photon or phonon scattering techniques can provide a significant advantage over electric and mechanical sensors 32. By way of example and not limitation, the entire structure 302 can be monitored using a single fiber optic cable 20 instead of deploying multiple sensors 32 in rail 302. Reliability can be improved if no sensors 32 are deployed in rail 302, using reflected photons from the light travelling into fiber optic cable 20 instead.

Additionally, the present invention may be used to monitor the status of the structure to assure that the stresses exerted onto the structure is within design specifications. The structure can be new or existing facility and the distributed fiber sensing system of the present invention can be attached to the structure to monitor desired parameters such as pressure, strain, stress and temperature.

By way of further example, traffic on a bridge, highway, or rail system 302 may be monitored using the present invention's sensorless technologies. The strain and vibration of the structure as different system pass through the structure will cause a reaction by the structure that can be detected as a signature of the device causing the stress or vibration. The information can be processed to determine amount of traffic on a road or rails 304.

Additionally, in a further exemplary embodiment, the present invention may be used with pipelines deployed undersea, pipelines deployed on a seabed, pipelines deployed on a non-underwater surface, and pipelines buried in the ground in a manner similar to the manner in which it may be used with railroad, highway, and similar systems.

It will be understood that various chances in the details, materials, and arrangements of the parts which have been described and illustrated above in order to explain the nature of this invention may be made by those skilled in the art without departing from the principle and scope of the invention as recited in the following claims.

What is claimed is:

1. A system for monitoring physical parameters distributed in a structure, comprising:
   a. a distributed optical sensing device (30), comprising a fiber optic cable (20,22), deployed proximate a predetermined structure, the fiber optic cable (20,22) being encapsulated in a jacket;
   b. a light source (18a) operatively in communication with the fiber optic cable (20,22);
   c. a light detection device (18b), operatively in communication with the fiber optic cable (20,22), for measuring the light received at the light detection device (18b) from the fiber optic cable (20,22); and
   d. a data processor (18) operatively connected to the light detection device (18b);

e. wherein:
   (i) the data processor (18) uses light measured at the light detection device (18b) to calculate a desired physical parameter distributed in the structure;
   (ii) the structure is a downhole structure comprising at least one of (a) a wellbore (10), (b) production tubing, (b) casing (12), and (d) non-production tubing;
   (iii) the physical parameter comprises parameters of at least one of (a) the wellbore (10), (b) production tubing, (c) non-production tubing, (d) a geological formation, and (e) casing (12); and
   (iv) the distributed optical sensing device (30) is integrated within a downhole component deployed permanently or temporarily in the wellbore (10) to measure at least one of (a) a physical parameter of the well, (b) drilling of and production from the well, or (c) geological formation parameters.

2. The system of claim 1 wherein at least one fiber optic cable (20,22) comprises fiber optic cable (20,22) optimized for use undersea and capable of measuring physical parameters over a predetermined portion of a length of the fiber optic cable (20,22).

3. The system of claim 2 wherein the fiber optic cable (20,22) is deployed undersea.

4. The system of claim 3 wherein the physical parameters comprise predetermined physical characteristics of methane hydrate.

5. A method for monitoring a predetermined set of physical characteristics associated with a structure or a process involving the structure, for a monitoring system, distributed in the structure, the method comprising:
   a. deploying a distributed optical sensing device (30) proximate a structure;
   b. providing light to the distributed optical sensing device (30) from a light source (18a);
   c. providing continuous light from a source of continuous light;
   d. providing pulsed light from a pulsed light probe beam;
   e. measuring light from the distributed optical sensing device (30) incident at a light detection device (18b) with the light detection device (18b);
   f. using a data processor (18) to substantially simultaneously obtain and continuously monitor a plurality of measurements from the distributed optical sensing device (30) at a plurality of locations along the distributed optical sensing device (30) using the measured light incident at the light detection device (18b);
   g. determining Brillouin loss;
   h. using the Brillouin loss to obtain the desired physical parameter measurements; and
   i. calculating a predetermined set of physical characteristics for a desired physical parameter using the plurality of measurements.

6. The method of claim 5 further comprising:
   i. stepping the continuous light source and the pulsed light probe beam through a range of frequencies around an anticipated Brillouin frequency and measuring power loss at each frequency;
   ii. determining a Brillouin shift at a frequency where a highest power loss is encountered; and
   iii. determining a desired physical parameter measurement by using a predetermined relationship between power loss and desired signal amplitude.

7. The method of claim 5, further comprising monitoring construction processes of the structure wherein step (e) further comprises calculating a progression of the construction of the structure using the one or more desired physical parameters.

8. The method of claim 5, wherein the structure is a downhole structure, further comprising:
   a. deploying the distributed optical sensing device (30) in the downhole structure in conjunction with a drilling, production, or fishing apparatus; and
   b. obtaining measurements using the distributed optical sensing device (30), the measurements comprising measurements of:
      i. parameters comprising borehole and geological parameters as a drilling or hydrocarbon production apparatus traverses formations during construction of a wellbore (10) wherein the borehole and geological parameters comprise pressures of formations through which the borehole proceeds and temperature of the formations;
      ii. production of fluids from formations in the wellbore (10) wherein the parameters comprise pressures of the formations and temperature of the formations;
      iii. strain on drilling pipe deployed in the structure;
      iv. parameters calculated from data obtained while drilling wherein noise created by a drilling process or external acoustic source located at a remote location generates an acoustic signal capable of traveling through geological formations proximate the structure, the noise being detected by the fiber optic cable (20,22) as the light from the light source (18a) travels through the fiber optic cable (20,22) by using reflected phonos or photons to determine information related to temperature, strain, pressure, and acoustic disturbances;
      v. corrosion of casing (12) or tubing deployed within the structure;
      vi. parameters comprising production parameters required to optimize production in intelligent wells;
      vii. parameters comprising production and physical parameters in laterals to determine optimum parameters, the optimum parameters further comprising pressure and flow, useful for production of hydrocarbons;
      viii. parameters comprising production and physical parameters in laterals to monitor production in the laterals where at least one lateral is divided in multiple zones isolated by downhole hardware including Intelligent Completion Systems;
      ix. parameters obtained from data measurements in abandoned wells useful to determine presence of leaks within formations in the well;
      x. parameters obtained from data measurements in wells useful to monitor compaction and subsidence of formations through which the structure passes;
      xi. parameters obtained from data measurements during artificial lift applications, the parameters comprising pressure, strain, flow, fluid identification, and temperature, the parameters useful to optimize production in gas lift, rod pump, progressive cavity pump, and electrical submersible pump applications;
      xii. parameters obtained from data measurements in injector wells to monitor movement of injected fluid or steam into the structure to assure that injected fluid reaches its proper destination in the structure;
      xiii. parameters obtained from data measurements in geothermal wells, the parameters comprising pressure, strain, and temperature; and
      xiv. parameters obtained from data measurements in multilateral wells comprising laterals wherein each lateral is monitored.

9. The method of claim 5 wherein the distributed optical sensing device (30) is deployed on a seabed to monitor a desired set of physical characteristics of the seabed, the set of physical characteristics comprising movement of the seabed, temperature of the seabed, and predetermined characteristics of methane hydrate present proximate the seabed useful in evaluating methane hydrate stability subsea.

10. The method of claim 5, wherein the structure is a downhole structure, further comprising:
   a. deploying the distributed optical sensing device (30) in the downhole structure in conjunction with a drilling, production, or fishing apparatus; and
   b. obtaining measurements using the distributed optical sensing device (30), the measurements comprising measurements of at least one of:
      i. parameters comprising borehole and geological parameters as a drilling or hydrocarbon production apparatus traverses formations during construction of a wellbore (10) wherein the borehole and geological parameters comprise pressures of formations through which the borehole proceeds and temperature of the formations;
      ii. production of fluids from formations in the wellbore (10) wherein the parameters comprise pressures of the formations and temperature of the formations;
      iii. strain on drilling pipe deployed in the structure;
      iv. parameters calculated from data obtained while drilling wherein noise created by a drilling process or external acoustic source located at a remote location generates an acoustic signal capable of traveling through geological formations proximate the structure, the noise being detected by the fiber optic cable (20,22) as the light from the light source (18a) travels through the fiber optic cable (20,22) by using reflected photons to determine information related to temperature, strain, pressure, and acoustic disturbances;
      v. corrosion of casing (12) or tubing deployed within the structure;
      vi. parameters comprising production parameters required to optimize production in intelligent wells;
      vii. parameters comprising production and physical parameters in laterals to determine optimum parameters, the optimum parameters further comprising pressure and flow, useful for production of hydrocarbons;
      viii. parameters comprising production and physical parameters in laterals to monitor production in the laterals where at least one lateral is divided in multiple zones isolated by downhole hardware including Intelligent Completion Systems;
      ix. parameters obtained from data measurements in abandoned wells useful to determine presence of leaks within formations in the well;
      x. parameters obtained from data measurements in wells useful to monitor compaction and subsidence of formations through which the structure passes;
      xi. parameters obtained from data measurements during artificial lift applications, the parameters comprising pressure, strain, flow, fluid identification, and temperature, the parameters useful to optimize production in gas lift, rod pump, progressive cavity pump, and electrical submersible pump applications;
      xii. parameters obtained from data measurements in injector wells to monitor movement of injected fluid or steam into the structure to assure that injected fluid reaches its proper destination in the structure;
      xiii. parameters obtained from data measurements in geothermal wells, the parameters comprising pressure, strain, and temperature; or
      xiv. parameters obtained from data measurements in multilateral wells comprising laterals wherein each lateral is monitored.

* * * * *